(12) United States Patent
Beeckler et al.

(10) Patent No.: US 11,737,818 B2
(45) Date of Patent: Aug. 29, 2023

(54) HEAT TRANSFER DURING ABLATION PROCEDURES

(71) Applicant: Biosense Webster (Israel) Ltd., Yokneam (IL)

(72) Inventors: Christopher Thomas Beeckler, Brea, CA (US); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 877 days.

(21) Appl. No.: 16/103,806

(22) Filed: Aug. 14, 2018

(65) Prior Publication Data
US 2020/0054390 A1   Feb. 20, 2020

(51) Int. Cl.
*A61B 18/14*    (2006.01)
*A61L 31/08*    (2006.01)
(Continued)

(52) U.S. Cl.
CPC ........ *A61B 18/1492* (2013.01); *A61L 31/088* (2013.01); *A61B 2017/00526* (2013.01);
(Continued)

(58) Field of Classification Search
CPC ...... A61B 18/1492; A61B 2018/00148; A61B 2018/0016; A61B 2018/1405; A61B 2018/00595; A61B 18/14; A61B 2018/1432; A61B 2017/00526; A61B 2018/00029; A61B 2018/00077; A61B 2018/00083; A61B 2018/00351; A61B 2018/00577; A61B 2218/002; A61B 2217/007; A61B 2018/1472; A61B 18/12; A61B 2018/00005; A61B 2018/1467; A61L 31/088; A61L 2420/02; C23F 1/04
See application file for complete search history.

(56) References Cited

U.S. PATENT DOCUMENTS 8,456,182 B2   6/2013   Bar-Tal et al.
2001/0021866 A1   9/2001   Dobak et al.
(Continued)

FOREIGN PATENT DOCUMENTS

WO   WO-2014066470 A1 *   5/2014   ........ A61M 25/0009

OTHER PUBLICATIONS

EPO EESR issued in EP 19191518.0, dated Oct. 21, 2019, 7 pages.

*Primary Examiner* — Linda C Dvorak
*Assistant Examiner* — Lindsay Regan Lancaster
(74) *Attorney, Agent, or Firm* — Lewis Roca Rothgerber Christie LLP

(57) ABSTRACT

Described embodiments include an apparatus that includes an intrabody probe and an electrode coupled to a distal end of the intrabody probe. The electrode includes a flexible electrically-insulating substrate, comprising a substrate surface. The electrode further includes a layer of an electrically-conducting metal covering at least part of the substrate surface. The electrode further includes a metallic sheet, comprising an inner sheet surface, and an outer sheet surface shaped to define multiple depressions. The electrode further includes an adhesive, which fills the depressions and bonds the outer sheet surface to the layer of the electrically-conducting metal. Other embodiments are also described.

27 Claims, 9 Drawing Sheets

(51) Int. Cl.
*A61B 17/00* (2006.01)
*A61B 18/00* (2006.01)
*C23F 1/04* (2006.01)

(52) U.S. Cl.
CPC ............ *A61B 2018/0016* (2013.01); *A61B 2018/00029* (2013.01); *A61B 2018/00077* (2013.01); *A61B 2018/00083* (2013.01); *A61B 2018/00148* (2013.01); *A61B 2018/00351* (2013.01); *A61B 2018/00577* (2013.01); *A61B 2218/002* (2013.01); *A61L 2420/02* (2013.01); *C23F 1/04* (2013.01)

(56) References Cited

U.S. PATENT DOCUMENTS

| | | | |
|---|---|---|---|
| 2002/0045893 A1 | 4/2002 | Lane et al. | |
| 2005/0038420 A1* | 2/2005 | Huybregts | A61F 7/123 606/20 |
| 2005/0222564 A1* | 10/2005 | Plaza | A61B 18/1492 606/41 |
| 2006/0100618 A1* | 5/2006 | Chan | A61B 18/1492 606/41 |
| 2006/0129061 A1* | 6/2006 | Kaneto | A61M 25/0043 600/561 |
| 2008/0156437 A1* | 7/2008 | Kawate | H05K 3/361 156/330 |
| 2008/0292898 A1* | 11/2008 | Straza | B32B 15/043 428/574 |
| 2009/0024015 A1* | 1/2009 | Curry | A61B 5/14546 600/347 |
| 2009/0143651 A1* | 6/2009 | Kallback | H05K 1/0274 600/301 |
| 2011/0014060 A1* | 1/2011 | Bolcavage | F01D 5/20 416/241 R |
| 2013/0105212 A1* | 5/2013 | Tsuboi | H05K 3/4046 174/264 |
| 2014/0058386 A1 | 2/2014 | Clark et al. | |
| 2014/0276758 A1 | 9/2014 | Lawrence et al. | |
| 2014/0328000 A1* | 11/2014 | Riddell | A01M 29/26 361/232 |
| 2014/0336640 A1* | 11/2014 | Beeckler | A61B 18/1492 606/41 |
| 2015/0272669 A1 | 10/2015 | Brucker et al. | |
| 2015/0273184 A1 | 10/2015 | Scott et al. | |
| 2016/0184008 A1* | 6/2016 | Papaioannou | A61B 5/6852 606/41 |
| 2016/0270732 A1 | 9/2016 | Källbäck et al. | |
| 2017/0311829 A1 | 11/2017 | Beeckler et al. | |
| 2018/0110562 A1 | 4/2018 | Govari et al. | |
| 2019/0117296 A1 | 4/2019 | Govari et al. | |
| 2019/0357972 A1 | 11/2019 | Beeckler et al. | |

\* cited by examiner

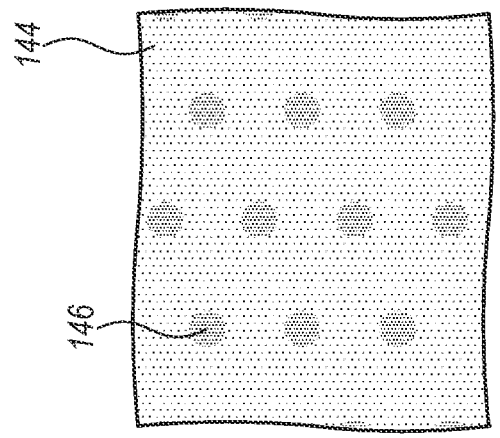
FIG. 6A
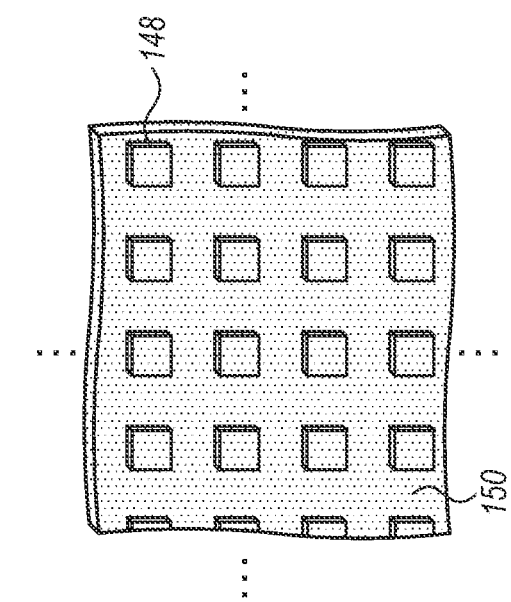
FIG. 6B
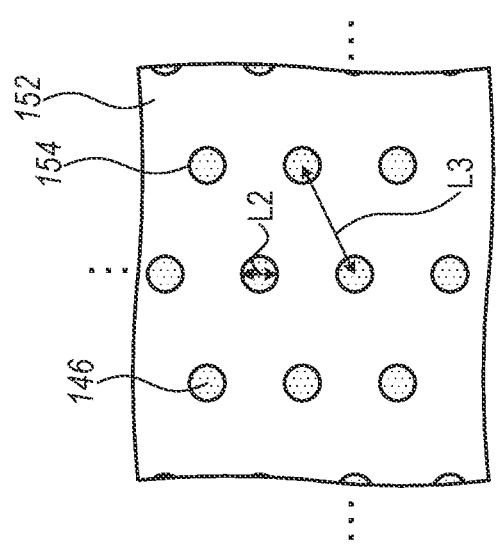
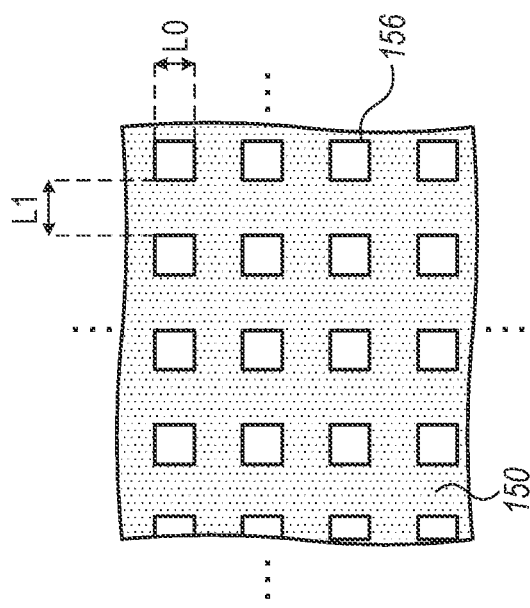

HEAT TRANSFER DURING ABLATION PROCEDURES

FIELD OF THE INVENTION

The present invention is related to intrabody probes and the use thereof in ablation procedures.

BACKGROUND

In some ablation procedures, an electrode disposed at the distal end of an intrabody probe is brought into contact with tissue, and radiofrequency (RF) energy is then passed from the electrode into the tissue. The RF energy raises the temperature of the tissue, thus creating lesions in the tissue.

US Patent Application Publication 2018/0110562, whose disclosure is incorporated herein by reference, describes a catheter that includes an insertion tube, a flexible substrate, and one or more electrical devices. The insertion tube is configured for insertion into a patient body. The flexible substrate is configured to wrap around a distal end of the insertion tube and includes electrical interconnections. The electrical devices are coupled to the flexible substrate and are connected to the electrical interconnections.

SUMMARY OF THE INVENTION

There is provided, in accordance with some embodiments of the present invention, an apparatus that includes an intrabody probe and an electrode coupled to a distal end of the intrabody probe. The electrode includes a flexible electrically-insulating substrate, including a substrate surface. The electrode further includes a layer of an electrically-conducting metal covering at least part of the substrate surface. The electrode further includes a metallic sheet, including an inner sheet surface, and an outer sheet surface shaped to define multiple depressions. The electrode further includes an adhesive, which fills the depressions and bonds the outer sheet surface to the layer of the electrically-conducting metal.

In some embodiments, the substrate and the sheet are shaped to define an interior lumen that is at least partly enclosed by the inner sheet surface.

In some embodiments, the substrate and the sheet are shaped to define a thimble.

In some embodiments, the distal end of the probe includes a flow diverter configured to divert fluid received from a proximal end of the probe, and the inner sheet surface is coupled to the flow diverter such that the flow diverter is disposed inside of the interior lumen.

In some embodiments, the substrate and the sheet are shaped to define a ring.

In some embodiments, the substrate and the sheet are shaped to define an arc.

In some embodiments, the sheet includes cobalt chromium.

In some embodiments, the electrically-conducting metal includes gold.

In some embodiments, each of the depressions has a circular perimeter.

There is further provided, in accordance with some embodiments of the present invention, a method that includes forming multiple depressions in an outer surface of a metallic sheet, and, subsequently to forming the depressions in the outer surface, applying an adhesive between the outer surface and a layer of an electrically-conducting metal that covers at least part of a substrate surface of a flexible electrically-insulating substrate, such that the adhesive fills the depressions and bonds the outer surface to the layer of the electrically-conducting metal. The method further includes, subsequently to applying the adhesive, coupling the metallic sheet to a distal end of an intrabody probe.

In some embodiments, forming the depressions includes forming the depressions by:
 coupling a mask, which is shaped to define a plurality of apertures, to the outer surface of the metallic sheet, and
 placing the metallic sheet into a chemical etching bath, such that portions of the outer surface exposed by the apertures are etched away.

In some embodiments, each of the apertures is circular.

There is further provided, in accordance with some embodiments of the present invention, an apparatus that includes an intrabody probe and an electrode coupled to a distal end of the intrabody probe. The electrode includes a flexible electrically-insulating substrate, including a substrate surface. The electrode further includes a layer of an electrically-conducting metal covering at least part of the substrate surface. The electrode further includes a metallic sheet, including an outer sheet surface bonded to the layer of the electrically-conducting metal, and an inner sheet surface shaped to define multiple protrusions.

In some embodiments, the substrate and the sheet are shaped to define an interior lumen that is at least partly enclosed by the inner sheet surface.

In some embodiments, the substrate and the sheet are shaped to define a thimble.

In some embodiments, the distal end of the probe includes a flow diverter configured to divert fluid received from a proximal end of the probe, and the inner sheet surface is coupled to the flow diverter such that the flow diverter is disposed inside of the interior lumen.

In some embodiments, the substrate and the sheet are shaped to define a ring.

In some embodiments, the substrate and the sheet are shaped to define an arc.

In some embodiments, the sheet includes cobalt chromium.

In some embodiments, the electrically-conducting metal includes gold.

In some embodiments, a perimeter of each of the protrusions is rectangular.

In some embodiments, a perimeter of each of the protrusions is star-shaped.

There is further provided, in accordance with some embodiments of the present invention, a method that includes forming multiple protrusions on an inner surface of a metallic sheet, and, subsequently to forming the protrusions on the inner surface, bonding an outer surface of the metallic sheet to a layer of an electrically-conducting metal that covers at least part of a substrate surface of a flexible electrically-insulating substrate. The method further includes, subsequently to bonding the outer surface of the metallic sheet to the layer of the electrically-conducting metal, coupling the metallic sheet to a distal end of an intrabody probe.

In some embodiments, forming the protrusions includes forming the protrusions by:
 coupling multiple masks to the inner surface, and
 placing the metallic sheet into a chemical etching bath, such that one or more portions of the inner surface, which are disposed between the masks, are etched away.

In some embodiments, each of the masks is rectangular.

In some embodiments, each of the masks is star-shaped.

There is further provided, in accordance with some embodiments of the present invention, a method that includes inserting, into a body of a subject, an electrode that includes (i) a flexible electrically-insulating substrate, including a substrate surface, (ii) a layer of an electrically-conducting metal covering at least part of the substrate surface, and (iii) a metallic sheet, including an outer sheet surface bonded to the layer of the electrically-conducting metal, and an inner sheet surface shaped to define multiple protrusions. The method further includes, subsequently to inserting the electrode into the body of the subject, passing an electric current between the electrode and another electrode, such that the electric current generates heat in tissue of the subject, and the heat is transferred to the protrusions. The method further includes causing a fluid to flow over a surface of the protrusions, such that the heat is transferred from the protrusions to the fluid.

In some embodiments, the fluid includes saline.

In some embodiments, the fluid includes blood of the subject.

In some embodiments, causing the fluid to flow over the surface of the protrusions includes causing the fluid to flow turbulently over the surface of the protrusions.

The present invention will be more fully understood from the following detailed description of embodiments thereof, taken together with the drawings, in which:

BRIEF DESCRIPTION OF THE DRAWINGS

FIG. 6A is a schematic illustration of a method for forming depressions in a surface of a supporting sheet, in accordance with some embodiments of the present invention;

FIG. 6B is a schematic illustration of a method for forming protrusions on a surface of a supporting sheet, in accordance with some embodiments of the present invention.

DETAILED DESCRIPTION OF EMBODIMENTS

Overview

Figure 1:
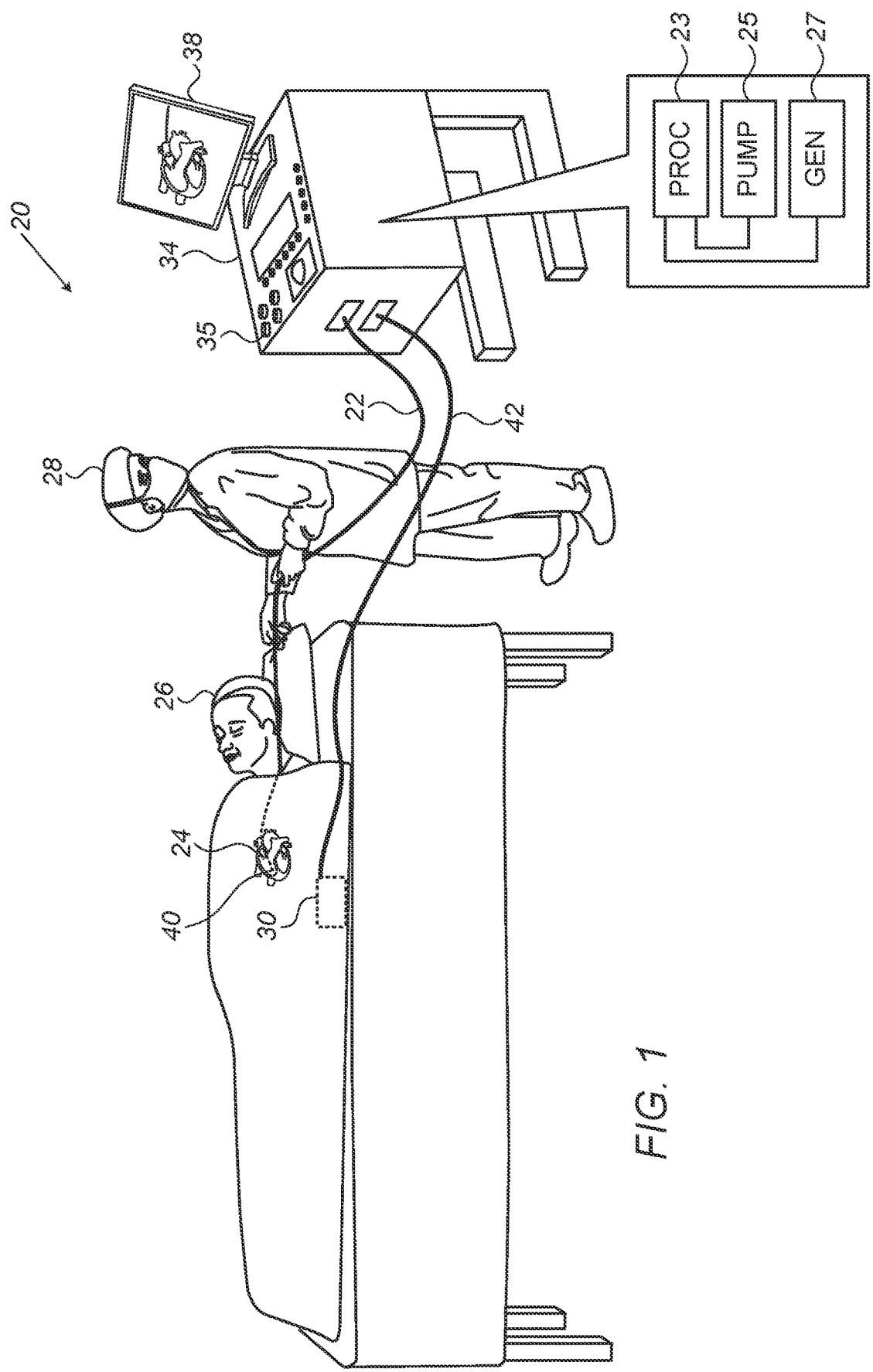
FIG. 1 is a schematic illustration of a system for ablating tissue of a subject, in accordance with some embodiments of the present invention.

As described in U.S. application Ser. No. 15/990,532, whose disclosure is incorporated herein by reference, embodiments of the present invention include an ablation electrode comprising at least one flexible printed circuit board (PCB) that is bonded, by an adhesive, to a supporting metallic sheet. (The supporting sheet may also be referred to as a "supporting structure.") The flexible PCB comprises a flexible electrically-insulating substrate comprising an outer surface that is coated by an outer layer of an electrically-conducting (and biocompatible) metal, such as gold, palladium, or platinum, and an inner surface that is coated by an inner layer of the same (and/or another) electrically-conducting metal. The inner surface may further support one or more electric components such as sensors (e.g., thermocouples) and traces, which are electrically isolated from the inner metallic layer. Following the deposition of the electric components, the coating of the substrate, and the bonding of the PCB to the supporting sheet, the flexible PCB (together with the supporting sheet) may be deformed into any suitable shape. For example, in some embodiments, the flexible PCB is deformed into a thimble-shaped electrode, referred to hereinbelow as a "tip electrode." The electrode is then coupled to the distal end of an intrabody probe.

During an ablation procedure, the outer metallic layer is brought into contact with the tissue that is to be ablated, and ablating currents are then passed, via the outer metallic layer, into the tissue. While the ablating currents are applied to the tissue, the sensors may acquire any relevant physiological readings from the tissue. Typically, open, plated vias, which pass through the electrode, provide electrical connectivity between the inner and outer metallic layers, such that the ablating currents may pass outward through the plated vias, and electrographic signals from the tissue may pass inward through the plated vias. Electrical connectivity may also be provided by blind vias, each such via being formed by the removal of a portion of the substrate, such that the outer metallic layer directly contacts a trace underneath.

The aforementioned plated vias also provide fluid communication between the inner and outer surfaces of the electrode, such that an irrigating fluid (e.g., saline) may pass through the plated vias into the surrounding blood. The irrigating fluid evacuates heat from the interior of the electrode into the blood, and additionally dilutes the blood at the tissue-electrode interface, thus reducing the probability of coagulum or charring. Due to the fact that the plated vias provide for passage of the irrigating fluid therethrough, the plated vias may also be referred to as "irrigation channels" or "irrigation holes."

Typically, a large number of small, closed vias, referred to hereinbelow as "thermal vias," pass through the substrate. The thermal vias increase the thermal connectivity between the inner and outer coatings of the substrate, such that more heat may be transferred from the tissue-electrode interface to the interior of the electrode. However, despite the thermal vias, the amount of heat evacuated by the irrigating fluid may be limited, due to the lack of sufficient surface area for heat exchange between the supporting sheet and the irrigating fluid. Moreover, the adhesive that bonds the PCB to the supporting sheet may provide significant thermal resistance, thus limiting the amount of heat that is transferred to the supporting sheet.

To address this challenge, embodiments described herein shape the inner surface of the supporting sheet, which contacts the irrigating fluid, to define multiple protrusions. Typically, the protrusions are formed by placing a pattern of masks over the inner surface of the supporting sheet, and then etching away the portions of the inner surface between the masks. The protrusions provide an increased surface area for contact with the irrigating fluid, and further cause turbulence in the flow of the irrigating fluid, thus increasing the amount of time during which the irrigating fluid contacts the inner surface. Hence, by virtue of the protrusions, more heat may be evacuated from the supporting sheet.

Alternatively or additionally, multiple depressions may be formed in the outer surface of the supporting sheet, which bonds to the PCB. For example, a pattern of circular depressions may be formed by placing a mask, which is shaped to define a pattern of circular holes, over the outer surface, and then etching away the portions of the outer surface that are exposed by the holes. These depressions collect the adhesive while the supporting sheet is bonded to the PCB, thus improving the adhesion between the supporting sheet and the PCB, while also reducing the amount of adhesive that interposes between the supporting sheet and the PCB outside of the depressions. As a result, more heat may be transferred to the supporting sheet.

System Description

Reference is initially made to FIG. 1, which is a schematic illustration of a system 20 for ablating tissue of a subject 26, in accordance with some embodiments of the present invention.

FIG. 1 depicts a physician 28 performing an ablation procedure on subject 26, using an intrabody probe 22. In this procedure, physician 28 first inserts an ablation electrode 40, disposed at the distal end of probe 22, into the subject, and then navigates electrode 40 to the tissue that is to be ablated. For example, the physician may advance the electrode through the vasculature of the subject until the electrode is in contact with cardiac tissue belonging to the heart 24 of the subject. Next, while electrode 40 contacts the tissue, the physician causes radiofrequency (RF) electric currents to be passed between the ablation electrode and another electrode, such that the electric currents generate heat in the tissue. For example, in a unipolar ablation procedure, the electric currents may be passed between the ablation electrode and a neutral electrode patch 30 that is coupled externally to the subject, e.g., to the subject's back.

To facilitate navigating probe 22, the probe may comprise one or more electromagnetic position sensors, which, in the presence of an external magnetic field, generate signals that vary with the positions of the sensors. Alternatively or additionally, any other suitable tracking system, such as an impedance-based tracking system, may be used. For example, both electromagnetic tracking and impedance-based tracking may be used, as described, for example, in U.S. Pat. No. 8,456,182, whose disclosure is incorporated herein by reference.

Probe 22 is proximally connected to a console 34, comprising, for example, a processor (PROC) 23, a pump 25, and a signal generator (GEN) 27. (Electrode patch 30 is typically also connected to console 34, via a wire 42.) During the ablation procedure, signal generator 27 generates the aforementioned ablating currents. These currents are carried through probe 22, over one or more wires, to electrode 40. Additionally, pump 25 supplies an irrigating fluid, such as saline, to the distal end of the probe, as further described below with reference to FIGS. 2A-B and FIG. 3.

Console 34 further comprises controls 35, which may be used by the physician to control the parameters of the ablating currents. In particular, in response to the manipulation of controls 35 by physician 28, processor 23 may adjust the parameters of the ablating currents, by outputting appropriate instructions to signal generator 27 over any suitable wired or wireless communication interface. Processor 23 may similarly control pump 25 over any suitable wired or wireless interface. In addition, the processor may receive and process any relevant signals from the distal end of the probe, such as the signals received from any of the sensors described herein.

In some embodiments, system 20 further comprises a display 38, which may display relevant output to physician 28 during the procedure.

Notwithstanding the particular type of procedure depicted in FIG. 1, it is noted that the embodiments described herein may be applied to any suitable type of ablation procedure (such as an otolaryngological or neurological ablation procedure), or any other procedure that necessitates the transfer of heat through a flexible PCB, such as the evacuation of heat from a circuit board into a surrounding fluid.

The Ablation Electrode

Figure 2A:
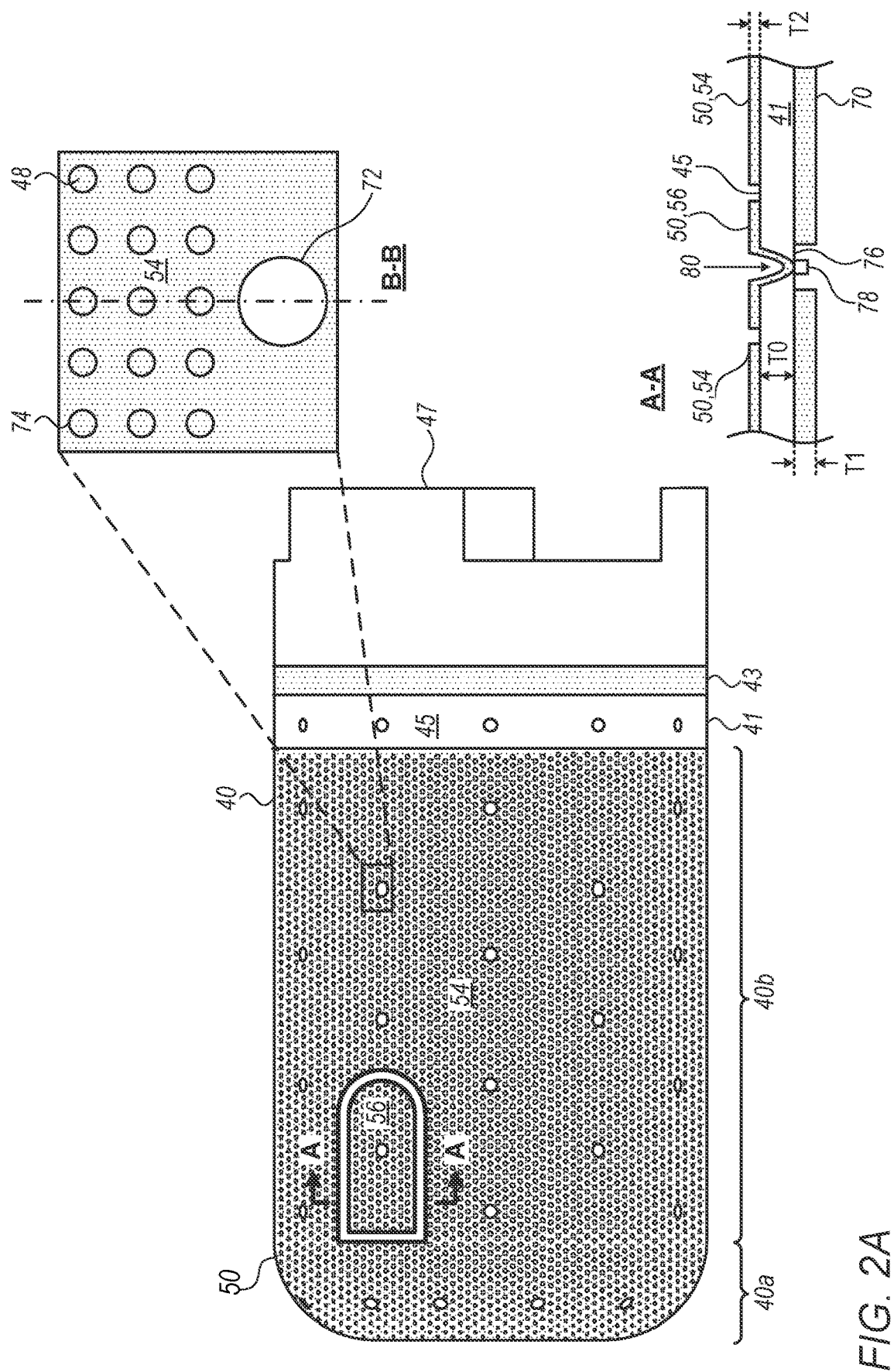
FIG. 2A is a schematic illustration of an ablation electrode, in accordance with some embodiments of the present invention.
Figure 3:
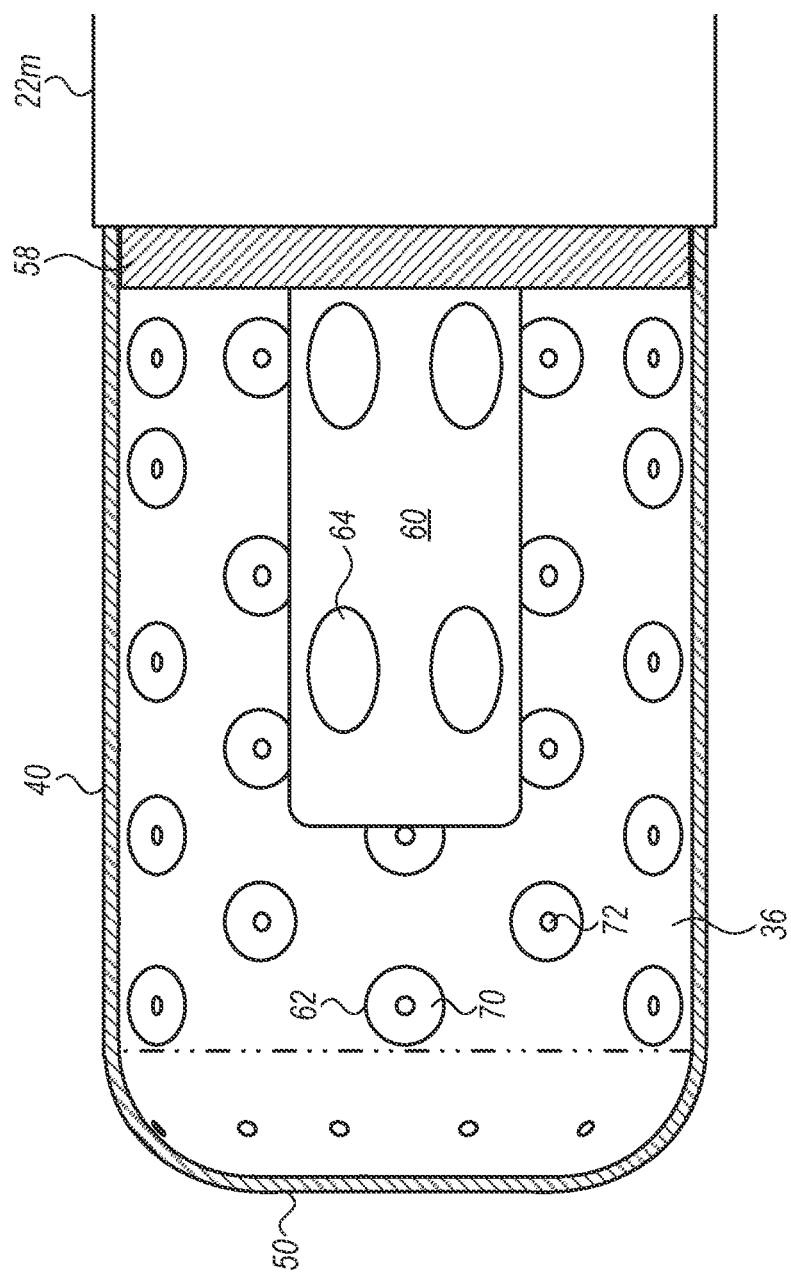
FIG. 3 schematically illustrates a longitudinal cross-section through the ablation electrode shown in FIG. 2A, in accordance with some embodiments of the present invention.

Reference is now made to FIG. 2A, which is a schematic illustration of ablation electrode 40, in accordance with some embodiments of the present invention. Reference is additionally made to FIG. 3, which schematically illustrates a longitudinal cross-section through electrode 40, in accordance with some embodiments of the present invention.

As described above with reference to FIG. 1, probe 22 comprises at least one ablation electrode 40, such as the tip electrode depicted in FIG. 2A and FIG. 3. Electrode 40 comprises a plated flexible electrically-insulating substrate 41 that is bonded, by an adhesive, to a supporting sheet 36 at the distal end of probe 22. Substrate 41 may be made of any suitable flexible electrically-insulating material, such as a flexible polymer (e.g., polyimide) or liquid crystal polymer (LCP). Supporting sheet 36 may be made of any suitably strong material, such as cobalt chromium, stainless steel, or magnesium. For example, the supporting sheet may comprise an alloy of cobalt chromium, such as the L-605 cobalt-chromium-tungsten-nickel alloy.

In general, electrode 40 may have any suitable shape. In some embodiments, as shown in FIG. 2A and FIG. 3, electrode 40 is thimble-shaped, comprising a cylindrical portion 40b that is capped by a dome-shaped portion 40a. Typically, tabs 47 at the proximal end of the electrode comprise soldering pads onto which wires, which run through the length of the probe, may be soldered, such as to establish electrical connectivity between the electrode and the proximal end of the probe. These soldering pads are described in further detail below, with reference to FIGS. 4-5.

As shown in the "A-A" cross-section of FIG. 2A, substrate 41 comprises an inner surface 76, which faces supporting sheet 36, and an outer surface 45, which faces away from supporting sheet 36. Typically, the thickness T0 of the substrate—i.e., the distance between the inner and outer surfaces of the substrate—is between 5 and 75 (e.g., between 12 and 50) microns. At least part of the inner surface is covered by an inner layer 70 of an electrically-conducting metal, such as gold. Typically, inner layer 70 has a thickness T1 of between 10 and 50 microns. Similarly, at least part of outer surface 45 is covered by an outer layer 50 of the metal. Typically, outer layer 50 has a thickness T2 of between 1 and 5 microns.

Typically, outer layer 50 is discontinuous, in that the outer layer comprises a main portion 54 along with one or more isolated portions that are electrically isolated from main portion 54 by exposed portions of the substrate. These isolated portions may include one or more "islands" that function as sensing microelectrodes 56. For example, outer layer 50 may comprise 3-7 microelectrodes 56 distributed around the circumference of the distal tip. Alternatively or additionally, the isolated portions may comprise a sensing ring electrode 43, which may be disposed, for example, near the proximal end of electrode 40.

A respective electrically-conductive trace 78, which is electrically isolated from inner layer 70 by an exposed portion of inner surface 76, is disposed beneath each of the sensing electrodes. As further described below with reference to FIG. 4, prior to forming the sensing electrodes, holes, referred to herein as blind vias 80, are formed (e.g., drilled) in the substrate above traces 78. Subsequently, as the sensing electrodes are deposited onto the outer surface of the substrate, the sensing electrodes at least partly fill blind vias 80, thus contacting the traces. Hence, during the procedure, electrographic signals from the cardiac tissue of the subject that are sensed by the sensing electrodes may be carried over traces 78 to wires that run through probe 22 to the proximal end of the probe. The signals may thus be delivered to processor 23 for analysis.

Figure 2B:
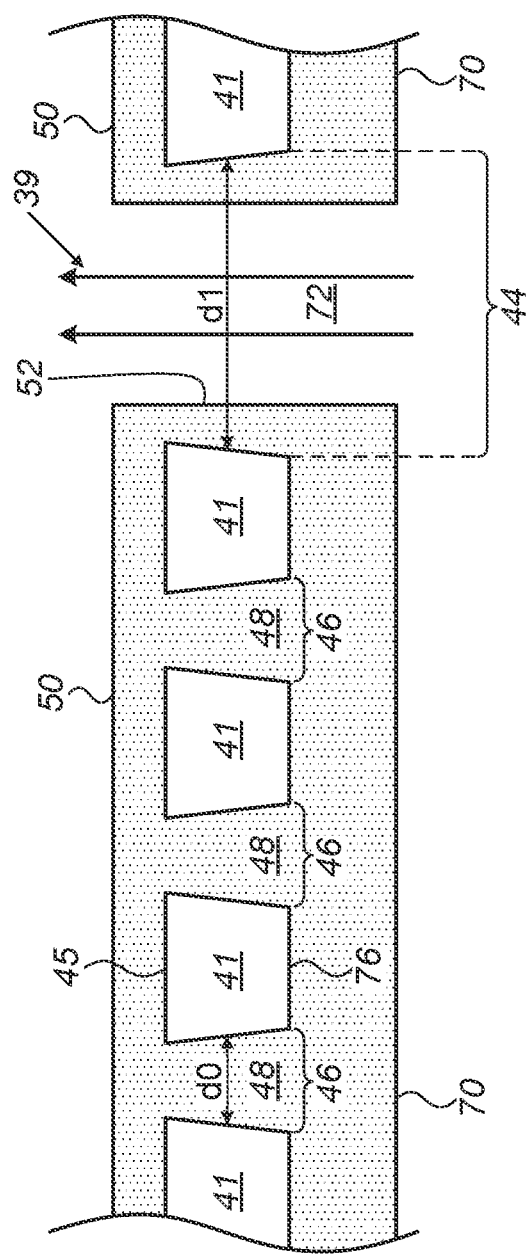
FIG. 2B is a schematic illustration of vias that pass through the surface of an ablation electrode, in accordance with some embodiments of the present invention.

Reference is now additionally made to FIG. 2B, which is a schematic illustration of vias that pass through the surface of electrode 40, in accordance with some embodiments of the present invention. FIG. 2B corresponds to the "B-B" cross-section indicated in FIG. 2A.

Substrate 41 is shaped to define a plurality of channels, including multiple narrower channels 46 and one or more wider channels 44, that pass between the inner and outer surfaces of the substrate. Typically, each channel is tapered along the length of the channel, with the cross-sectional area of the channel at the inner surface of the substrate being slightly greater than the cross-sectional area at the outer surface. The cross-sectional area (or average cross-sectional area) of each narrower channel 46 is less than that of each wider channel 44.

In some embodiments, the channels have a circular cross-section. In such embodiments, the average diameter d0 of each of the narrower channels may be less than 50% (e.g., less than 25%) of the average diameter d1 of each of the wider channels. Alternatively or additionally, diameter d0 may be between 5 and 50 (e.g., between 5 and 30) microns, and/or diameter d1 may be between 50 and 300 microns. In other embodiments, at least some of the channels may have a cross-section having a square shape, or any other suitable shape. (In such embodiments, the average cross-sectional area of each of the channels may correspond to that implied above by the ranges for d0 and d1.)

Typically, the electrode includes 30-100 wider channels. Each wider channel 44 is plated by a plating layer 52 of the electrically-conducting metal, which connects outer layer 50 to inner layer 70. The plated wider channels thus provide electrical and thermal conductivity between the outer and inner layers of metal. Moreover, the plated wider channels provide a fluid passageway between the interior and exterior of the electrode, such that an irrigating fluid 39, supplied by pump 25 (FIG. 1), may flow therethrough. Hence, the plated wider channels may be referred to as "irrigation holes" 72. (The diameter of each irrigation hole is smaller than diameter d1 by approximately twice the thickness of plating layer 52.) Supporting sheet 36 is shaped to define apertures 62 that are aligned with irrigation holes 72, such that the supporting sheet does not obstruct the irrigation holes.

Typically, the number of narrower channels 46 is relatively large. For example, substrate 41 may be shaped to define at least 1,000, 5,000, 10,000, or 20,000 narrower channels. Alternatively or additionally, the ratio of narrower channels to wider channels may be at least 300:1. Alternatively or additionally, the total area of the respective outer openings of the narrower channels (i.e., the openings of the narrower channels at the outer surface of the substrate) may be at least 10%, 20%, or 30% of the area of the outer surface of the substrate. Thus, for example, if the area of the outer surface of the substrate (including the narrower channels) is 27 mm$^2$, and each of the narrower channels includes a circular outer opening having a diameter of 25 microns (and hence an area of 0.0005 mm$^2$), the number of narrower channels may be approximately 16,500 (for a total area of 8.1 mm$^2$), such that the outer openings of the narrower channels cover approximately 30% of the outer surface.

In contrast to the wider channels, narrower channels 46 are not merely plated, but rather, are filled by respective columns 48 of the electrically-conducting metal, which connect outer layer 50 to inner layer 70. (Columns 48 are not necessarily cylindrical, since, as noted above, narrower channels 46 do not necessarily have a circular cross-section. Furthermore, as noted above, the cross-sectional area of each column may vary along the length of the column. It is noted that outer layer 50, inner layer 70, plating layer 52 and columns 48 may be collectively described as a single body of metal that covers the substrate.) Due to the large number of channels 46, and by virtue of each of these channels being filled, a large amount of heat may be transferred via channels 46. Hence, the filled narrower channels may be referred to as "thermal vias" 74. (For ease of illustration, no thermal vias are shown in the "A-A" cross section of FIG. 2A.)

Notwithstanding the above, it is noted that in some embodiments, the narrower channels are not filled, but rather, are merely plated, similarly to the wider channels. Even in such embodiments, a large amount of heat may be transferred to the interior of the electrode.

Typically, probe 22 comprises a fluid-delivery tube (not shown), which runs through the full length of the tubular body 22m of probe 22. The fluid-delivery tube is distally coupled to a flow diverter 60 that is shaped to define one or more fluid-flow apertures 64. Flow diverter 60 diverts fluid 39, which is received, via the fluid-delivery tube, from the proximal end of the probe, through fluid-flow apertures 64. In such embodiments, electrode 40 may be coupled to the base 58 of flow diverter 60, such that the flow diverter is disposed inside of the interior lumen of the electrode. For example, supporting sheet 36 may be bonded to base 58. Alternatively or additionally, base 58 may be shaped to define a plurality of protrusions and supporting sheet 36 may be shaped to define a plurality of complementary holes, such that the protrusions snap into the holes.

As described above with reference to FIG. 1, during the ablation procedure, physician 28 contacts tissue of subject 26 with electrode 40, and in particular, with outer layer 50. While contacting the tissue with outer layer 50, the physician passes electric currents, via the outer layer, into the tissue. The electric currents cause heat to be generated in the tissue, such that a lesion is formed in the tissue. This heat is transferred, via thermal vias 74 (i.e., via columns 48) to inner layer 70. At the same time, pump 25 (FIG. 1) pumps irrigating fluid 39 through the fluid-delivery tube, such that the fluid flows into the interior of the electrode through fluid-flow apertures 64 of flow diverter 60. This fluid then flows out of the electrode through apertures 62 and irrigation holes 72, thus evacuating the heat from inner layer 70 into the subject's blood.

Manufacturing the Ablation Electrode

Figure 4:
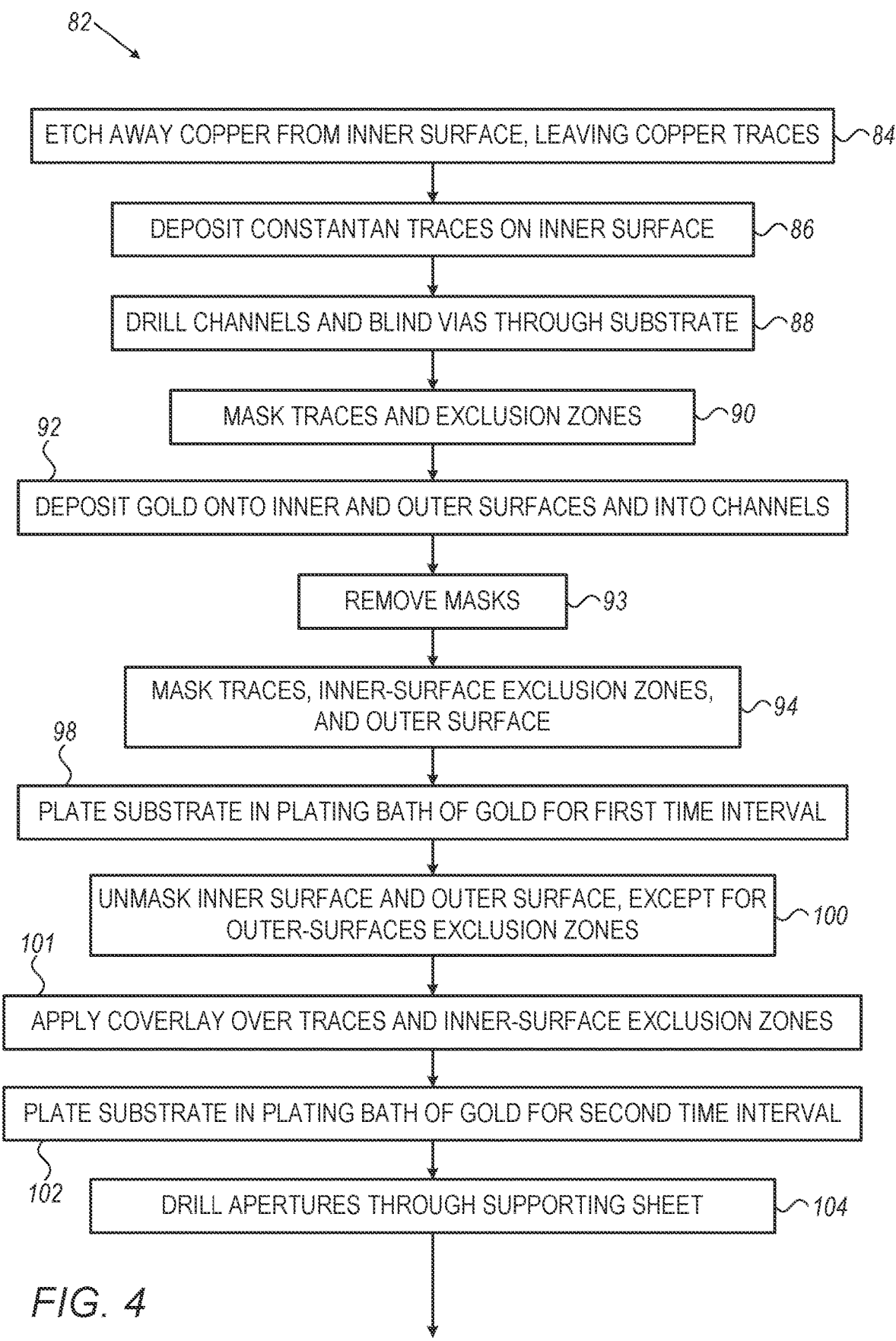
FIG. 4 is a flow diagram for a method of manufacturing an ablation electrode, in accordance with some embodiments of the present invention.
Figure 4:
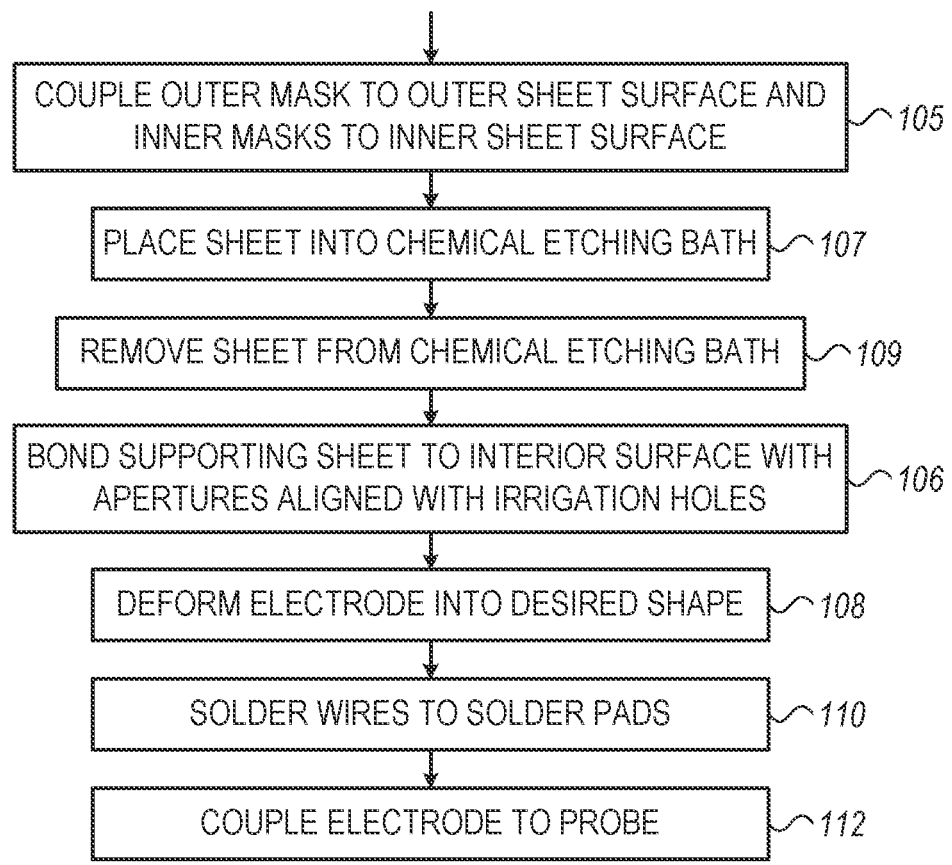
Figure 5:
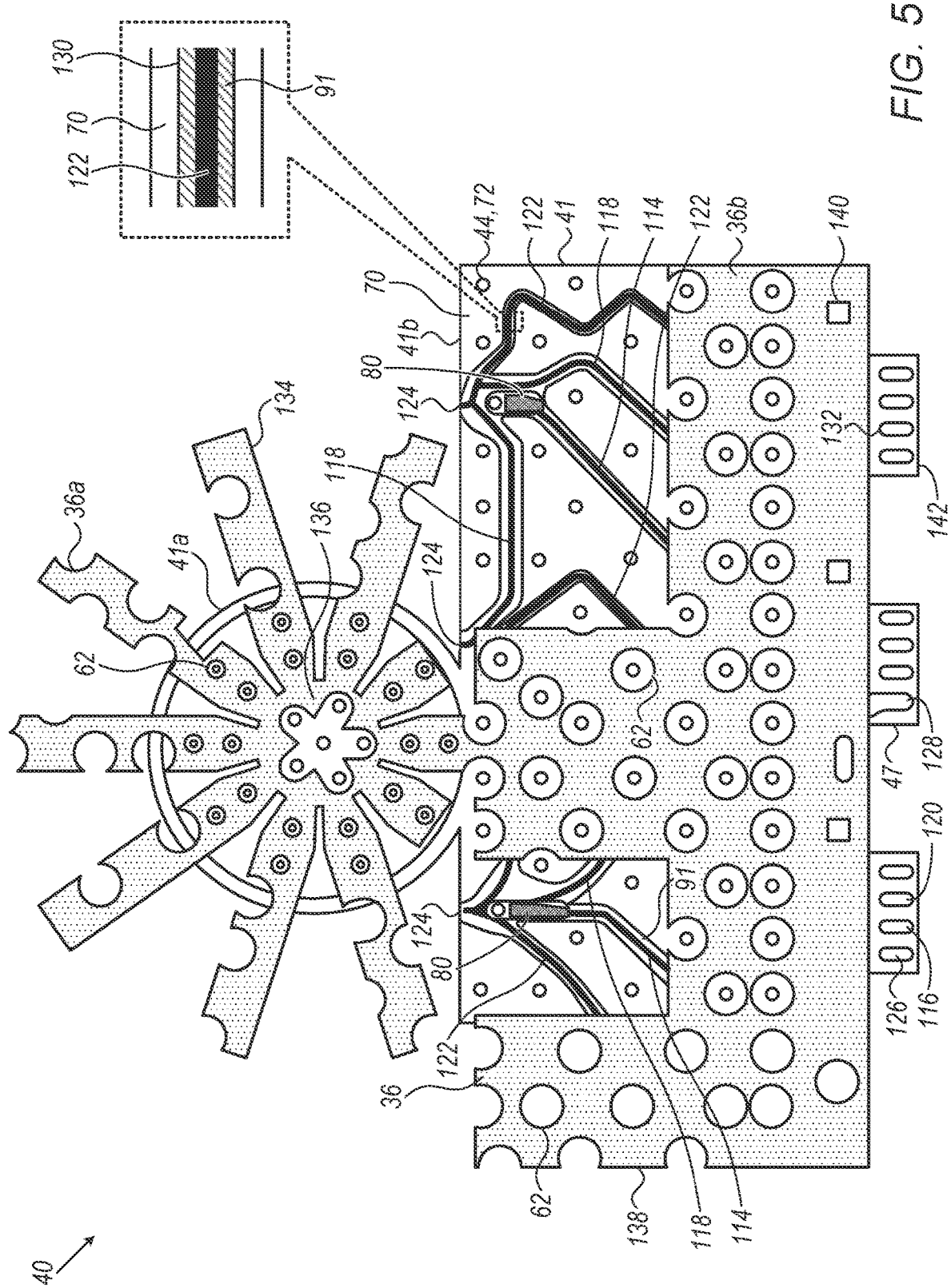
FIG. 5 is a schematic illustration of an ablation electrode prior to the deformation thereof, in accordance with some embodiments of the present invention.

Reference is now made to FIG. 4, which is a flow diagram for a method 82 of manufacturing electrode 40, in accordance with some embodiments of the present invention. Reference is additionally made to FIG. 5, which is a schematic illustration of electrode 40 prior to the deformation thereof, in accordance with some embodiments of the present invention. (FIG. 5 shows the interior of electrode 40, i.e., the various elements that are coupled to the inner surface of substrate 41.)

FIG. 4 assumes that at least the inner surface of the substrate is initially coated with a layer of copper. Hence, method 82 begins with an etching step 84, in which all of the copper is etched away from the inner surface, with the exception of copper traces 114, which are to be connected to the sensing electrodes on the exterior of the electrode. (Any copper on the outer surface is also etched away.) This etching may be performed, for example, by placing a mask over the portions of the copper that are designated for traces 114, and then chemically removing the exposed copper. Alternatively, if the inner surface of the substrate is initially exposed, copper traces 114 may be deposited onto the inner surface.

Subsequently, at a trace-depositing step 86, constantan traces 118, which are to be used for thermocouples, are deposited onto the inner surface of the substrate. Trace-depositing step 86 may be performed, for example, by physical vapor deposition (PVD), such as sputter deposition. For example, a mask may be placed over the entire inner surface, with the exception of those portions of the inner surface that are designated for constantan traces 118. Subsequently, a seed layer of a base metal, such as titanium-tungsten, may be sputtered onto the substrate. Finally, the constantan may be sputtered over the base metal.

Typically, to minimize the required wiring, the constantan traces terminate at a common constantan-trace soldering pad 120. In some embodiments, prior to the deposition of the constantan, a hole (or "stake via") is drilled through the substrate at the site of soldering pad 120. Subsequently, the deposited constantan fills the hole, and then forms soldering pad 120 above the hole. Alternatively, instead of drilling completely through the substrate, a depression may be drilled into the substrate, such that the deposited constantan fills the depression. In either case, soldering pad 120 is "staked" to the substrate by the constantan underneath the soldering pad. (To facilitate the filling of the hole or depression, a draft angle may be used to taper the hole or depression, as described immediately below for the narrower and wider channels.)

Next, at a drilling step 88, multiple narrower channels and one or more wider channels 44 are drilled through the substrate, typically using laser drilling. (The wider channels, but not the narrower channels, may be seen in FIG. 5.) Typically, the channels are drilled from the inner surface of the substrate, using a draft angle such that the channels narrow as they approach the outer surface; this facilitates the collection of metal onto the walls of the channels during the subsequent sputtering process. In addition, blind vias 80 may be drilled (e.g., laser-drilled) through the substrate from the outer surface of the substrate at those portions of the outer surface that are designated for sensing electrodes, using copper traces 114 as stops. (In other words, portions of the substrate that are disposed over the copper traces may be removed, thus exposing the copper traces.) Typically, a draft angle is used for the blind vias, such that the blind vias narrow as they approach the inner surface of the substrate; this facilitates the collection of metal onto the walls of the blind vias.

Next, at a first masking step 90, the copper and constantan traces, along with exclusion zones 91 (i.e., exposed portions of the inner surface of the substrate) that are designated for insulating these traces, are masked. (Portions of the constantan traces that are designated for the thermocouple junctions are not masked.) Additional exclusion zones designated for insulating the gold traces that will intersect the constantan traces (thus forming constantan-gold thermocouples) are also masked. Additionally, exclusion zones on the outer surface that are designated for insulating the sensing electrodes are masked.

Subsequently, at a depositing step 92, a thin layer of gold is deposited onto the inner and outer surfaces of the substrate and into the channels. Depositing step 92 may be performed, for example, by physical vapor deposition (PVD), such as sputter deposition. (Typically, a seed layer of a base metal, such as titanium-tungsten, is sputtered onto the substrate prior to the sputtering of the gold.) By virtue of the masks, the gold is not deposited onto the traces or exclusion zones.

The deposited gold includes an initializing layer for inner layer 70, outer layer 50, plating layer 52, and columns 48. The deposited gold further includes gold traces 122 that cover the constantan traces at thermocouple junctions 124. Each gold trace 122 terminates at a respective gold-trace soldering pad 126. The deposited gold further includes a respective copper-trace soldering pad 116 for each of the copper traces. In some embodiments, copper-trace soldering pads 116 and/or gold-trace soldering pads 126 are staked to the substrate, as described above for the constantan-trace soldering pad. The deposited gold further includes at least one gold soldering pad 128, which is connected to inner layer 70. Gold soldering pad 128 may also be staked to the substrate.

Following the deposition, the masks (along with any gold that was deposited onto the masks) are removed at a mask-removing step 93. Subsequently, at a second masking step 94, the traces, the inner-surface exclusion zones that surround the traces, and the entire outer surface of the substrate are masked.

Following second masking step 94, while the traces and outer surface remain masked, the substrate is plated in a plating bath of gold for a first time interval, at a first plating step 98. The plating of the substrate causes any gaps in the gold to be filled, and further increases the thickness of the gold, such that, for example, inner layer 70 reaches a thickness of between 5 and 40 microns, while the diameter of the wider channels is reduced to between 30 and 200 microns. Additionally, the narrower channels may become completely filled.

Typically, the plating of the substrate is electrochemical, whereby the flow of electric current through the gold that already coats the substrate causes this gold to attract gold ions in the plating bath. The amplitude and duration of the current may be controlled such that the gold reaches the desired thickness.

Following first plating step 98, the inner and outer surfaces of the substrate, with the exception of the aforementioned exclusion zones designated to insulate the sensing electrodes, are unmasked, at an unmasking step 100. Next, at a coverlay-applying step 101, at least one coverlay 130 is applied over the traces and inner-surface exclusion zones. (In some embodiments, as illustrated in the inset portion of FIG. 5, coverlay 130 is transparent or nearly transparent.)

Typically, the proximal portion of coverlay 130 that covers tabs 47 is shaped to define windows 132 that expose the soldering pads, such that the soldering pads may be thickened during the subsequent plating process. (An additional cover 142, having windows that are aligned with windows 132, may cover the proximal portion of the coverlay.) Typically, the soldering pads are not completely exposed, but rather, are held "captive" by coverlay 130, in that one or more edges of each soldering pad are covered by the rims of windows 132. Coverlay 130 thus helps hold the soldering pads to substrate 41 during the subsequent soldering process.

Subsequently, at a second plating step 102, the substrate is plated in the plating bath for a second time interval, such that any gaps in outer layer 50 are filled, while the inner, outer, and plating layers are thickened. For example, the second plating may increase the thickness of the inner layer to between 10 and 50 microns, while reducing the diameter of the wider channels to between 15 and 150 microns. Typically, the final thickness of the inner layer is the same as the thickness of the coverlay, such as to attain a smooth interior surface. (To avoid any confusion, the term "interior surface" is used herein to refer to the surface that is formed by the coverlay and the inner gold layer, whereas the term "inner surface" is used to refer to the underlying surface of the substrate.) Additionally, in the event that the narrower channels were not completely filled during first plating step 98, these channels are completely filled during second plating step 102. As in the case of first plating step 98, the amplitude and duration of the electric current in the plating bath may be controlled such that the desired thicknesses are attained.

(In some embodiments, the outer surface is masked prior to depositing step 92, such that no gold is deposited onto the outer surface during depositing step 92. In such embodiments, following unmasking step 100 and prior to second plating step 102, a thin layer of gold is deposited onto the outer surface.)

Subsequently to second plating step 102, at an aperture-drilling step 104, apertures 62 are drilled through supporting sheet 36. (Alternatively to drilling, any other suitable technique, such as chemical etching, may be used to form the apertures.)

Reference is now additionally made to FIG. 6A, which is a schematic illustration of a method for forming depressions in a surface of supporting sheet 36, in accordance with some embodiments of the present invention. Reference is also made to FIG. 6B, which is a schematic illustration of a method for forming protrusions on another surface of supporting sheet 36, in accordance with some embodiments of the present invention.

Following aperture-drilling step 104, as shown in FIGS. 6A-B, multiple depressions 144 are formed in the outer surface 146 of supporting sheet 36 (i.e., the surface of the sheet designated for bonding to the PCB), and/or multiple protrusions 148 are formed on the inner surface 150 of the sheet. To form depressions 144, an outer mask 152, which is shaped to define a plurality of mask apertures 154, is coupled to outer sheet surface 146. Subsequently, the sheet is placed into a chemical etching bath and is left in the bath for a predetermined duration of time, such that portions of outer sheet surface 146 exposed by mask apertures 154 are etched away. Similarly, to form protrusions 148, multiple inner masks 156 are coupled to inner sheet surface 150, and the sheet is then placed into a chemical etching bath and is left in the bath for a predetermined duration of time, such that the portions of the inner surface disposed between masks 156 are etched away.

Typically, both depressions 144 and protrusions 148 are formed. In some embodiments, the depressions and protrusions are formed simultaneously. (In such embodiments, the height of the protrusions is approximately equal to the depth of the depressions.) For example, returning to FIG. 4, at a third masking step 105, outer mask 152 may be coupled to the outer surface of the sheet, and inner masks 156 may be coupled to the inner surface of the sheet. Subsequently, at a chemical etching step 107, the sheet may be placed into the bath, such that both the depressions and protrusions are formed. Following the formation of the depressions and protrusions, the sheet is removed from the bath, at a sheet-removing step 109.

In other embodiments, the depressions and protrusions are formed at separate times. For example, during a first chemical etching step, the outer surface of the sheet may be masked by outer mask 152 while the inner surface of the sheet is completely masked, such that the depressions, but not the protrusions, are formed. Subsequently, during a second chemical etching step, the inner surface of the sheet may be masked by the inner masks while the outer surface of the sheet is completely masked, such that the protrusions are formed. Advantageously, this technique facilitates a protrusion height that is different from the depression depth, in that the respective durations of the two chemical etching steps may be made different from one another.

In some embodiments, each mask aperture 154 is circular, such that each depression 144 has a circular perimeter. In such embodiments, the diameter L2 of each mask aperture may be between 0.01 and 0.2 mm. Alternatively, some or all of the mask apertures may have any other suitable shape.

Mask apertures 154 (and hence, depressions 144) may be arranged in a grid pattern, or in any other suitable arrangement. For example, as shown in FIG. 6A, a plurality of circular mask apertures may be arranged in a close-packed pattern, with a distance L3 of between 0.05 and 0.5 mm between the respective centers of neighboring mask apertures. In some embodiments, L3 is approximately twice L2.

In some embodiments, each inner mask 156 is rectangular, such that (the inner surface of) each protrusion 148 has a rectangular perimeter. For example, each inner mask may be square-shaped, having a length L0 of between 0.01 and 0.2 mm. Alternatively, some or all of the inner masks may have any other suitable shape. For example, each inner mask may be star-shaped, such that the perimeter of (the inner surface of) each of the protrusions is star-shaped. Examples of such shapes—which provide a relatively large amount of surface area for contact with the irrigating fluid, and a large number of edges for generating turbulent flow—include those of N-pointed stars, where N is three or more.

Inner masks 156 (and hence, protrusions 148) may be arranged in any suitable arrangement, such as a grid pattern. For example, a plurality of square inner masks may be arranged in a grid, with a distance L1 of between 0.05 and 0.5 mm separating between neighboring squares. In some embodiments, the distance between neighboring squares is approximately equal to the length of each square, i.e., L1 is approximately equal to L0.

Figure 7:
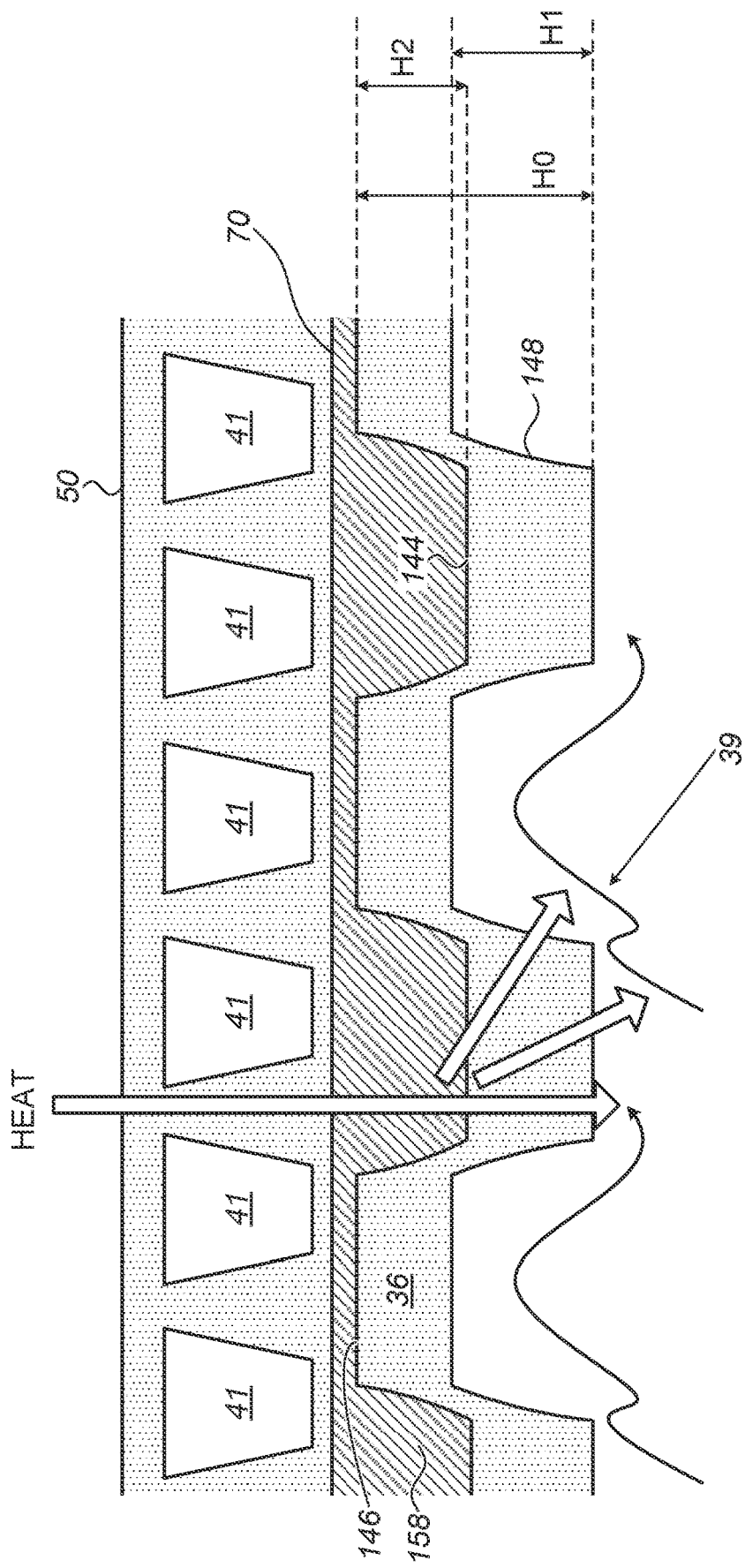
FIG. 7 schematically illustrates the transfer of heat to the interior of an ablation electrode, in accordance with some embodiments of the present invention.

Typically, the area of each aperture 154 is smaller than the area of each inner mask 156, and the inner masks are aligned with the outer masks such that the entire perimeter of each aperture is opposite a respective inner mask. (This reduces the risk of a thru-hole being accidentally formed during the chemical etching process.) As a result of this sizing and alignment, each of the depressions is entirely opposite a protrusion (as illustrated in FIG. 7, which is described below).

Alternatively to chemical etching, other techniques, such as laser etching, may be used to form protrusions 148 and/or depressions 144.

Following the formation of the depressions and/or protrusions, at a bonding step 106, an adhesive is applied between outer sheet surface 146 and the smooth interior surface that is formed by coverlay 130 and inner layer 70. The adhesive fills the depressions and bonds outer sheet surface 146 to the interior surface of the PCB. Typically, the supporting sheet is bonded to the interior surface such that apertures 62 are aligned with irrigation holes 72. Typically, the area of the apertures is greater than that of the irrigation holes, such as to compensate for any small misalignments when bonding the supporting sheet.

Next, at a deforming step 108, electrode 40 is deformed into the desired shape. For example, the electrode may be inserted into a forming jig that shapes the electrode around a suitable mandrel. Following the insertion of the electrode into the jig, the jig is placed inside an oven. Subsequently, the oven heats the electrode to a suitable temperature, while pressure is applied to the electrode. The combination of heat and pressure causes the electrode to bond to itself in the desired shape.

In general, the substrate and supporting sheet may be deformed into any desired shape. Typically, however, during deforming step 108, the substrate and supporting sheet are shaped to define an interior lumen that is at least partly enclosed by the inner surface of the sheet. For example, as described above with reference to FIG. 2A and FIG. 3, the substrate and supporting sheet may be shaped to define a thimble.

Typically, to facilitate the manufacture of a thimble-shaped electrode, substrate 41 comprises two portions that are continuous with one another: a distal, circular portion 41a, and a proximal, rectangular portion 41b. Similarly, supporting sheet 36 comprises two portions that are continuous with one another: a distal supporting portion 36a, typically comprising a plurality of spokes 134 that radiate from a central hub 136, and a proximal supporting portion 36b. During bonding step 106, distal supporting portion 36a is bonded to the interior surface of circular portion 41a, and the adhesive is applied to the outer surfaces of spokes 134. (These surfaces are opposite the surfaces shown in FIG. 5.) In addition, proximal supporting portion 36b is bonded to the interior surface of rectangular portion 41b, leaving some distal portions of this interior surface exposed. The adhesive is applied to the outer surface of an overhanging tab 138 of proximal supporting portion 36b, which hangs over the side of rectangular portion 41b. (Proximal supporting portion 36b may also hang over the proximal end of rectangular portion 41b.)

Subsequently, during deforming step 108, distal supporting portion 36a and circular portion 41a are folded over the top of the mandrel, while proximal supporting portion 36b and rectangular portion 41b are rolled around the mandrel. To maintain this configuration, the outer surfaces of spokes 134 are bonded to the exposed distal portions of the interior surface of rectangular portion 41b, and the outer surface of tab 138 is bonded to the opposite end of proximal supporting portion 36b. (Additionally, the inner surface of at least one of the spokes may bond to tab 138.) Thus, distal supporting portion 36a and circular portion 41a are formed into dome-shaped portion 40a (FIG. 2A), while proximal supporting portion 36b and rectangular portion 41b are formed into cylindrical portion 40b.

Subsequently, at a soldering step 110, wires are soldered onto the soldering pads. In particular, the wire that delivers RF currents from generator 27 (FIG. 1) is soldered onto gold soldering pad 128, while other wires, which deliver signals to processor 23, are soldered to the other soldering pads.

Finally, at a coupling step 112, the electrode is coupled to the probe. For example, proximal supporting portion 36b may be bonded to base 58 of the flow diverter (FIG. 3). Alternatively or additionally, as described above with reference to FIG. 3, protrusions belonging to base 58 may snap into complementary holes 140 in proximal supporting portion 36b. Subsequently, the flow diverter may be coupled to the fluid-delivery tube belonging to the probe. (Alternatively, the flow diverter may be coupled to the fluid-delivery tube before the electrode is coupled to the flow diverter.)

In other embodiments, the substrate and supporting sheet are shaped to define a ring or an arc. In some embodiments, a plurality of such ring-shaped and/or arc-shaped electrodes are coupled to each other at the distal end of the probe, so as to define a ball. By virtue of spaces between the rings and/or arcs, blood may flow through the ball during the ablation procedure. Hence, the heat generated from the ablation may be transferred from protrusions 148 directly to the blood of the subject.

In general, any suitable masking technique may be used at each of the steps in which a mask is required. Examples of suitable masks include liquid and film photoresists.

Alternatively or additionally to the traces described above, any other suitable electric or electronic components may be deposited onto the inner surface of the substrate. Such components may include thermistors for measuring the temperature of the tissue, pressure sensors for measuring the pressure applied to the distal end of the probe, and/or electromagnetic sensors for navigating the probe. These components (along with suitable surrounding exclusion zones) may be masked or covered whenever such masking or covering is required, as described above for the traces.

It is noted that the scope of the present disclosure includes any suitable modification to method 82 with respect to the order of the steps that are performed and/or with respect to the various materials that are used, as will be apparent to any person of skill in the art. For example, any suitable electrically-conducting metal may be used in lieu of copper, gold, or constantan.

Heat Transfer

Reference is now made to FIG. 7, which schematically illustrates the transfer of heat to the interior of electrode 40, in accordance with some embodiments of the present invention.

As described above with reference to FIG. 4, an adhesive 158 bonds supporting sheet 36 to the interior surface of the PCB. Advantageously, adhesive 158 fills depressions 144, thus improving the adhesion of the supporting sheet to the PCB, while also reducing the amount of adhesive that interposes between the undepressed portion of the outer sheet surface and the PCB. In other words, by virtue of the adhesive collecting in the depressions, outer sheet surface 146 may contact, or nearly contact, the interior surface of the PCB. As a result, more heat may be transferred to the supporting sheet, and in particular, to protrusions 148.

As further described above, during and/or following the application of the ablation currents, fluid 39 is made to flow over the surface of protrusions 148. By virtue of the large surface area provided by the protrusions, and/or by virtue of the turbulent flow caused by the protrusions, a large amount of heat is transferred from the protrusions to fluid 39. As described above with reference to FIG. 4, in some embodiments, the subject's blood, rather than fluid 39, flows over the surface of the protrusions, such that the heat is transferred from the protrusions directly to the blood.

In some embodiments, the height H1 of each protrusion, and/or the depth H2 of each depression, is between 5% and 60% of the thickness H0 of the sheet. (As described above with reference to FIG. 4, by forming the depressions and protrusions in two separate chemical etching steps, the depth of the depressions may be made different from the height of the protrusions.) For example, if H0 is between 0.025 and 0.2 mm, each of H1 and H2 may be between 0.00125 and 0.12 mm.

In general, the embodiments described herein may be combined with any of the embodiments described in US Patent Application Publication 2018/0110562 or U.S. patent application Ser. No. 15/793,126, whose respective disclosures are incorporated herein by reference.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
   (a) an intrabody probe; and
   (b) an electrode coupled to a distal end of the intrabody probe, the electrode comprising:
      (i) a flexible electrically-insulating substrate, comprising a substrate surface,
      (ii) a layer of an electrically-conducting metal covering at least part of the substrate surface,
      (iii) a metallic sheet, comprising:
         (A) an exposed inner sheet surface configured to transmit thermal energy to fluid, and
         (B) an outer sheet surface shaped to define multiple depressions, and
      (iv) an adhesive, which fills the depressions and bonds the outer sheet surface to the layer of the electrically-conducting metal.

2. The apparatus according to claim 1, the substrate and the sheet being shaped to define an interior lumen that is at least partly enclosed by the inner sheet surface.

3. The apparatus according to claim 2, the substrate and the sheet being shaped to define a thimble.

4. The apparatus according to claim 2, the distal end of the probe comprising a flow diverter configured to divert fluid received from a proximal end of the probe, and the inner sheet surface being coupled to the flow diverter such that the flow diverter is disposed inside of the interior lumen.

5. The apparatus according to claim 1, the substrate and the sheet being shaped to define a ring.

6. The apparatus according to claim 1, the substrate and the sheet being shaped to define an arc.

7. The apparatus according to claim 1, the sheet comprising cobalt chromium.

8. The apparatus according to claim 1, the electrically-conducting metal comprising gold.

9. The apparatus according to claim 1, each of the depressions having a circular perimeter.

10. Apparatus, comprising:
    (a) an intrabody probe; and
    (b) an electrode coupled to a distal end of the intrabody probe, the electrode comprising:
       (i) a flexible electrically-insulating substrate defining a plurality of channels, comprising a substrate surface,
       (ii) a layer of an electrically-conducting metal covering at least part of the substrate surface,
       (iii) a metallic sheet, comprising:
          (A) an inner sheet surface, and
          (B) an outer sheet surface shaped to alone define multiple concave depressions, and
       (iv) an adhesive, which fills the depressions and bonds the outer sheet surface to the layer of the electrically-conducting metal.

11. The apparatus of claim 10, each channel in the plurality of channels having a circular shape.

12. The apparatus of claim 11, having one channel of the plurality of channels being a wider channel compared to the rest of the channels in the plurality of channels.

13. The apparatus of claim 12, the wider channel having a plating layer.

14. The apparatus of claim 13, the plating layer being formed by the layer of an electrically-conducting metal.

15. The apparatus of claim 10, the plurality of channels being filled with the electrically-conducting metal.

16. Apparatus, comprising:
    (a) an intrabody probe; and
    (b) an electrode coupled to a distal end of the intrabody probe, the electrode forming a cylindrical shape, the electrode comprising:
       (i) a flexible electrically-insulating substrate, comprising a substrate surface,
       (ii) a layer of an electrically-conducting metal covering at least part of the substrate surface,
       (iii) a metallic sheet, comprising:
          (A) an inner sheet surface shaped to form multiple protrusions, the inner sheet surface being exposed to an interior of the electrode, and
          (B) an outer sheet surface shaped to define multiple depressions, the inner sheet surface facing away from the outer sheet surface, and
       (iv) an adhesive, which fills the depressions and bonds the outer sheet surface to the layer of the electrically-conducting metal.

17. The apparatus of claim 16, further comprising a flow diverter configured to distribute fluid onto the inner sheet surface.

18. Apparatus, comprising:
    (a) an intrabody probe; and
    (b) an electrode coupled to a distal end of the intrabody probe, the electrode comprising:
       (i) a flexible electrically-insulating substrate, comprising a substrate surface,
       (ii) a layer of an electrically-conducting metal covering at least part of the substrate surface,
       (iii) a metallic sheet, comprising:
          (A) an inner sheet surface, and
          (B) a single outer sheet surface comprising multiple concave surfaces shaped to define a respective depression, and
       (iv) an adhesive, which fills the depressions and bonds the outer sheet surface to the layer of the electrically-conducting metal, the adhesive being interposed between the metallic sheet and the layer of the electrically-conducting metal.

19. The apparatus of claim 18, the adhesive material being in direct contact with both the outer sheet surface and the layer of electrically-conducting metal.

20. The apparatus of claim 19, the inner sheet surface forming a plurality of protrusions.

21. The apparatus of claim 18, the electrode further comprising an ablation electrode.

22. The apparatus of claim 18, the intrabody probe being configured to connect to a console.

23. Apparatus, comprising:
(a) an intrabody probe; and
(b) an electrode coupled to a distal end of the intrabody probe, the electrode comprising:
  (i) a flexible electrically-insulating substrate, comprising a substrate surface,
  (ii) a layer of an electrically-conducting metal covering at least part of the substrate surface,
  (iii) a metallic sheet, comprising:
    (A) an exposed inner sheet surface having multiple protrusions, and
    (B) an outer sheet surface shaped to define multiple concave depressions facing away from the exposed inner sheet surface, and
  (iv) an adhesive, which fills the depressions and bonds the outer sheet surface to the layer of the electrically-conducting metal.

24. The apparatus of claim 23, the flexible electrically-insulating substrate comprising a flexible polymer.

25. The apparatus of claim 23, the flexible electrically-insulating substrate comprising a liquid crystal polymer.

26. The apparatus of claim 23, the flexible electrically-insulating substrate comprising a cylindrical portion.

27. The apparatus of claim 23, the metallic sheet comprising cobalt chromium.

* * * * *